United States Patent [19]

Christidis et al.

[11] 4,436,752

[45] Mar. 13, 1984

[54] TREATMENT OF GASTRIC AND GASTRO-DUODENAL DISORDERS WITH DERIVATIVES OF PHENYL ALIPHATIC CARBOXYLIC ACIDS

[75] Inventors: Yani Christidis; Robert Fournex, both of Paris, France

[73] Assignee: Roussel-UCLAF, Paris, France

[21] Appl. No.: 368,209

[22] Filed: Apr. 14, 1982

[30] Foreign Application Priority Data

Apr. 17, 1981 [FR] France ............................... 81 07802

[51] Int. Cl.³ .............................................. A61K 31/19
[52] U.S. Cl. ............................................... 424/317
[58] Field of Search ................. 424/308, 317; 562/463

[56] References Cited

U.S. PATENT DOCUMENTS

| | | | |
|---|---|---|---|
| 2,532,579 | 12/1950 | Thomas | 560/51 |
| 2,562,208 | 7/1951 | Papa et al. | 562/463 |
| 3,753,997 | 8/1973 | Ash et al. | 546/194 |
| 3,763,148 | 10/1973 | Ash et al. | 546/326 |
| 3,846,470 | 11/1974 | Raabe et al. | 424/250 X |
| 3,910,959 | 10/1975 | Vallet | 549/445 |
| 3,940,404 | 2/1976 | Ash et al. | 546/334 |
| 3,940,487 | 2/1976 | La Croix et al. | 424/282 |
| 3,953,463 | 4/1976 | Ash et al. | 546/326 |
| 4,017,517 | 4/1977 | Murata et al. | 549/436 |

FOREIGN PATENT DOCUMENTS

| | | |
|---|---|---|
| 1282644 | 9/1962 | Fed. Rep. of Germany . |
| 2047806 | 4/1972 | Fed. Rep. of Germany . |
| 2103749 | 8/1972 | Fed. Rep. of Germany . |
| 2501834 | 7/1975 | Fed. Rep. of Germany . |
| 1566212 | 5/1969 | France . |
| 1566213 | 5/1969 | France . |
| 2132354 | 12/1972 | France . |
| 2270856 | 12/1975 | France . |
| 55-36434 | 3/1980 | Japan . |
| 588108 | 6/1947 | United Kingdom . |
| 1387733 | 3/1975 | United Kingdom . |

OTHER PUBLICATIONS

*Journal of American Pharmaceutical Association*, vol. 37, No. 11, Nov. 1948, pp. 439-449.
*Chemical Abstracts*, vol. 88, No. 5, Jan. 30, 1978, Abstract 37442p.
*Journal of the American Chemical Society*, vol. 71, No. 4, Apr. 1949, F. K. Kirchner et al., pp. 1210-1213.
*Journal of the American Chemical Society*, vol. 70, No. 10, Oct. 1948, D. Papa et al., pp. 3356-3360.
*European Journal of Medical Chemistry Chimica Therapeutica*, vol. 12, Jan.-Feb. 1977, pp. 17-20.
*European Journal of Medical Chemistry Chimica Therapeutica*, vol. 13, No. 3, May-Jun. 1978, H. Orzalesi et al., pp. 259-264.
*Beilstein*, vol. 19, p. 312.
*Journal of Pharmaceutical Sciences*, vol. 66, No. 4, Apr. 1977, pp. 466-476, Child, Ralph G., et al., "Fenbufen, a New Anti-Inflammatory Analgesic: Synthesis and Structure-Activity Relationships of Analogs".
*Journal of Medicinal Chemistry*, vol. 15, No. 9, Sep. 1972, pp. 918-922, *Markovac*, A., et al., "Antimalarials. 3, 2,6-Bis(aryl)-4-pyridinemethanols with Trifluoromethyl Substituents".
*Journal of Organic Chemistry*, vol. 35, No. 5, May 1970, pp. 1367-1376, *Pettit*, George R., et al., "Bufadienolides. 1., Introduction and Base-Catalyzed Condensation of Methyl Ketonds with Glyoxylic Acid".
*J.A.C.S.*, vol. 46, No. 10, Oct. 1924, pp. 2319-2326, *Rice*, Grace Potter, "The Isomeric Esters of Para-Ethoxy-Benzoylacrylic Acid".

*Primary Examiner*—Leonard Schenkman
*Attorney, Agent, or Firm*—Stevens, Davis, Miller & Mosher

[57] ABSTRACT

Gastric and gastro-duodenal disorders are treated by administering a compound of formula (I)

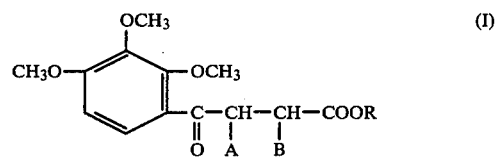

in which A and B together represent a double bond or else A represents a hydrogen atom and B represents a hydroxy radical, and in which R represents a hydrogen atom or an alkyl radical containing from 1 to 5 carbon atoms, in the various possible stereoisomeric forms, as well as the pharmaceutically acceptable alkali metal, alkaline earth metal or amine salts of the compound of formula (I) in which R represents a hydrogen atom.

4 Claims, No Drawings

TREATMENT OF GASTRIC AND GASTRO-DUODENAL DISORDERS WITH DERIVATIVES OF PHENYL ALIPHATIC CARBOXYLIC ACIDS

The present invention relates to the treatment of hyperchlorhydria, gastric and gastro-duodenal ulcers, gastritis, hiatal hernias, and gastric and duodenal ailments accompanied by gastric hyperacidity by administering a substituted derivative of phenyl butenoic or phenyl butanoic acid, and to pharmaceutical compositions containing those compounds.

Particularly, the present invention relates to administering compounds of the formula (I)

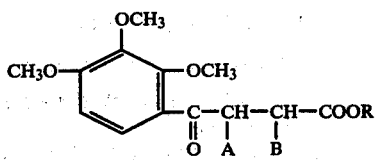

in which A and B together represent a double bond or else A represents a hydrogen atom and B represents a hydroxy radical, and in which R represents a hydrogen atom or an alkyl radical containing from 1 to 5 carbon atoms, in the various possible stereoisomeric forms, as well as the pharmaceutically acceptable alkali metal, alkaline earth metal or amine salts of the compound of formula (I) in which R represents a hydrogen atom.

The compound (E) 4-(2,3,4-trimethoxyphenyl)-4-oxo-2-butenoic acid is disclosed in French Patent No. 2,132,354 but no pharmacological properties or use in therapy has as yet been described for it. It has been discovered that this acid, as well as other compounds falling within formula (I), show substantial anti-ulcer activity. Furthermore, when brought into contact with the gastric mucosa they exhibit a gastric anti-secretory activity.

The expression "alkyl containing 1 to 5 carbon atoms" may, for example, designate a methyl, ethyl, n-propyl, isopropyl, n-butyl, isobutyl, ter-butyl or pentyl radical.

The different possible stereoisomeric forms in the case of compounds of formula I in which A and B together represent a double bond represent the geometrical isomers E and Z (trans and cis) and, in the case of compounds of formula I in which A represents a hydrogen atom and B represents a hydroxy radical, they represent the racemic and optically active forms of these last-mentioned compounds.

The alkali metal or alkaline earth metal salts of the compounds of formula I in which R represents a hydrogen atom may be sodium, potassium, lithium or calcium salts.

The amine salts of the compounds of formula I in which R represents a hydrogen atom are the ordinary amine salts. Among the customary amines mention may be made of the monoalkyl amines, such as, for instance, methyl amine, ethyl amine, propyl amine, the dialkylamines such as, for instance, dimethylamine, diethylamine, di-N-propylamine, and the trialkylamines such as triethylamine. Mention may also be made of piperidine, morpholine, piperazine and pyrrolidine.

A preferred compound for use in the present invention is (E) 4-(2,3,4-trimethoxyphenyl)-4-oxo-2-butenoic acid.

The dose to be administered to the patient, which varies in accordance with the compound used and the ailment concerned, may range for instance, between 0.05 and 2 g preferably between 0.2 g and 1.5 g per day per os for adults. As previously indicated, the present invention also concerns pharmaceutical compositions containing at least one compound of formula (I) as the active ingredient. These compositions can be prepared in a known manner so they can be administered by digestive or parenteral route.

They may be solid or liquid and be present in the pharmaceutical forms currently used in human medicine, such as, for instance, simple or sugar-coated tablets, capsules, granules, suppositories and injectable preparations; they are prepared by the customary methods.

The active principle or principles may be incorporated in the excipients customarily employed in these pharmaceutical compositions, such as talc, gum arabic, lactose, starch, magnesium stearate, cocoa butter, aqueous or non-aqueous vehicles, fatty substances of animal or vegetable origin, the paraffin derivatives, glycols, the various wetting, dispersing or emulsifying agents and preservatives.

(E) 4-(2,3,4-trimethoxyphenyl)-4-oxo-2-butenoic acid can be prepared by the methods indicated in French Patent No. 2,132,354, such as, for example, by alkaline hydrolysis of 2,3,4-trimethoxybenzoylacrylonitrile.

It may also be prepared by condensation of glyoxylic acid with 2,3,4-trimethoxyacetophenone in the presence of acetic anhydride at about 130° C. by a method similar to those described in Japanese Patent Application 77 39020 published on Oct. 3, 1977 (C.A. 88: 37442p), or in J.Med.Chem., 1972, Vol. 15, No. 9, 918–22.

As indicated in J.Med.Chem. 1972, Vol. 15, No. 9, 918–22 one can also proceed in two steps, by preparing a 4-phenyl-4-oxo-2-hydroxy butanoic acid substituted on the phenyl ring by condensation of the glyoxylic acid with an acetophenone substituted on the phenyl ring at about 80° C., and dehydration of the product obtained. Compounds of formula (I) have thus been prepared by effecting the condensation at about 95° C. and dehydrating the resultant product by a hot acid. Examples of such preparations are given below.

The alkali metal, alkaline-earth metal, or amine salts of compounds of formula I may be prepared, when not known, by a customary process such as, for instance, by action of the corresponding bases on the said compounds of formula I or by a double decomposition reaction.

The base may be an inorganic or organic base such as, for instance, sodium hydroxide, potassium hydroxide, lithium hydroxide, calcium hydroxide, sodium ethylate, potassium ethylate, ammonia or an amine such as, for example, methylamine, ethylamine, propylamine, dimethylamine, diethylamine, di-N-propylamine, triethylamine, piperadine, morpholine, piperazine or pyrrolidine.

The reaction is preferably carried out in a solvent or mixture of solvents such as water, ethyl ether, ethanol, acetone, or ethyl acetate.

The compounds of formula I in which R represents an alkyl radical containing from 1 to 5 carbon atoms which were not known can be prepared in the customary manner by action of an alcohol of formula ROH on the corresponding acid of formula I, preferably in acid medium. The acid may, for instance, be hydrochloric acid or phosphoric acid.

The cis products of formula I may be prepared by irradiating the corresponding trans products of formula I, as indicated in J.Org.Chem. 13, 1948, pages 284–296.

The examples presented below are for the purpose of illustrating the invention without, however, limiting it to the specific embodiments:

EXAMPLE 1

4-(2,3,4-trimethoxyphenyl)-4-oxo-2-hydroxy butanoic acid 25.2 g (0.17 mole) of glyoxylic acid, 50% by weight in water, are heated under reduced pressure until elimination of 80% of the water present, and then, after cooling, 71.5 g (0.34 mole) of 2,3,4-trimethoxyacetophenone are added and heating is effected for 150 minutes at 95° C. under reduced pressure (50 mm/Hg), at the same time distilling off the residual water present.

Then, after cooling the medium to room temperature, there are introduced 150 cc of ether and 200 cc of distilled water containing 10 g of pure dry sodium carbonate.

The mixture is allowed to settle out and the aqueous phase is washed with ether, whereupon the aqueous phase is acidified to a pH of 1 with 6 N hydrochloric acid. The desired product is then extracted with ethyl acetate. After washing, drying and elimination of the extraction solvent under reduced pressure, the desired product is isolated.

After recrystallization from dichloro-1,2-ethane, 18 g of the purified desired product are obtained.
MP=94° C.

Analysis: Calculated: C%, 54.93; H%, 5.67. Found: C%, 54.6; H%, 5.5. Acidimetry (expressed as percentage of the theoretical)=99.4% NMR spectrum: In accordance with the structure proposed.

EXAMPLE 2

(E) 4-(2,3,4-trimethoxyphenyl)-4-oxo-2-butenoic acid 9.5 g (0.033 M) of 4-(2,3,4-trimethoxyphenyl)-4-oxo-2-hydroxy butanoic acid, 15 cc of acetic acid and 1.5 cc of concentrated hydrochloric acid (d=1.18) are heated for two hours under reflux.

The solution obtained is then cooled to room temperature and then, after addition of water, the yellow precipitate which has formed is filtered off, giving 5.4 g of crude product.

After recrystallization from 25 cc of a mixture of acetic acid and water (1:3) there are obtained 4.6 g of (E) 4-(2,3,4-trimethoxy phenyl) 4-oxo-2 butenoic acid.
MP=100° C.

The product obtained was chromatographed on a silica gel column, eluting with a mixture of toluene (90), dioxane (16) and acetic acid (2).

The expected purified product is obtained.
MP=100° C.

Acidimetry (expressed as percentage of the theoretical)=100.4±0.5 NMR spectrum: In accordance with the structure proposed. Analysis: Calculated: C%, 58.64; H%, 5.30. C%, 58.6; H%, 5.4.

Pharmaceutical Forms

EXAMPLE 3

Tablets

Tablets of the following formula were prepared: (E) 4-(2,3,4-trimethoxyphenyl)-4-oxo-2 butenoic acid: 100 mg Excipient q.s. for a finished tablet of: 300 mg (details of the excipient: lactose, wheat starch, processed starch, rice starch, magnesium stearate, talc).

EXAMPLE 4

Capsules

Capsules of the following formula were prepared: (E) 4-(2,3,4-trimethoxyphenyl)-4-oxo-2-butenoic acid: 100 mg Excipient q.s. for a finished capsule of: 300 mg (details of the excipient: talc, magnesium stearate, aerosil).

PHARMACOLOGICAL STUDY (1) Determination of the anti-ulcer activity

The technique used is described by SHAY et al. in Gastroenterology, 5, 43 (1945).

SHAY's technique consists of inducing ulcers in rats at the level of the stomach by ligature of the pylorus.

The animals are anesthetized with ether. A longitudinal incision is made about 1 cm below the sternum, the glandular portion of the stomach and the duodenum are uncovered and a ligature is placed a few millimeters below the pylorus. The muscular plane is left as is and the skin is sutured by two clips.

The animals then immediately receive the dispersive or the substance to be studied per os in a volume of 0.5 ml/100 g, and are kept without food or drink until sacrificed by carotid section, effected about 16 hours after the treatment.

Before removing the stomach, a ligature is placed above the cardia.

The gastric fluid is collected in order to measure its pH.

The stomach is then opened along the greater curvature, rinsed in physiological serum and spread on graph paper in order to be examined under a binocular lens.

The severity of the lesions, graded from 0 to 4 for each stomach, is then evaluated macroscopically.

The average intensity of the ulcerations is determined for each lot of rats and the protection is calculated as the ratio of the mean index for the treated group to the mean index for the control group.

The pH of the gastric fluid is also determined for the treated animals and the control animals.

The following results were obtained:

TABLE 1

| Compound of example | Dose (mg/kg) | pH of the gastric fluid treated animals | pH of the gastric fluid control animals | Ulceration % protection, with respect to the controls |
|---|---|---|---|---|
| 1 | 100 | 3.3 | 2.7 | 41 |
| 2 | 20 | 5.8 | 3.2 | 99 |
|  | 4 | 3.7 | 3.2 | 76 |
|  | 0.8 | 3.1 | 3.5 | 17 |

(2) Determination of acute toxicity

The lethal dose $LD_{50}$ of the derivatives of Examples 1 and 2 was evaluated after administration by oral route to mice.

The results obtained are as follows:

TABLE 2

| Product of Example | LD$_{50}$ (mg/kg) |
|---|---|
| 1 | >1000 |
| 2 | ≃ 300 |

What is claimed is:

1. A method of treating a patient suffering from hyperchlorhydria, gastric or gastro-duodenal ulcers, gastritis, hiatal hernia, or gastric or gastro-duodenal ailments accompanied by gastric hyperacidity, comprising administering to said patient an anti-ulcer and anti-gastric secretory effective amount of a compound of the formula (I)

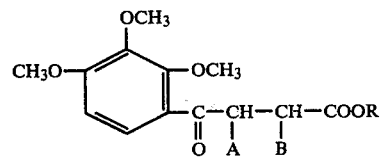

in which A and B together represent a double bond or else A represents a hydrogen atom and B represents a hydroxy radical, and in which R represents a hydrogen atom or an alkyl radical containing from 1 to 5 carbon atoms, in their racemic or optically active forms, and pharmaceutically acceptable salts of said compound wherein R represents a hydrogen atom.

2. A method according to claim 1 wherein A and B together represent a double bond in their cis or trans forms and said salts are selected from the group consisting of alkali metal, alkaline earth metal and amine salts.

3. A method according to claim 1 wherein the compound of formula I is (E) 4-(2,3,4-trimethoxyphenyl)-4-oxo-2-butenoic acid.

4. A method according to claim 1 wherein the compound of formula I is 4-(2,3,4-trimethoxyphenyl)-4-oxo-2-hydroxy butanoic acid.

* * * * *